United States Patent [19]

Elias et al.

[11] Patent Number: 4,654,124

[45] Date of Patent: Mar. 31, 1987

[54] PURIFYING CUMENE HYDROPEROXIDE

[75] Inventors: Carole L. Elias, Plum Boro; Marvin C. Fields, Wilkins Township, Allegheny County, both of Pa.

[73] Assignee: Aristech Chemical Corporation, Pittsburgh, Pa.

[21] Appl. No.: 841,984

[22] Filed: Mar. 20, 1986

Related U.S. Application Data

[63] Continuation-in-part of Ser. No. 780,756, Sep. 27, 1985, abandoned.

[51] Int. Cl.$^4$ .................... B01D 1/22; C07C 179/04
[52] U.S. Cl. ........................................ 203/72; 203/73; 203/80; 159/49; 568/576
[58] Field of Search ............... 203/72, 6, 73, 80, 89, 203/91, 95, 92; 568/576; 159/49, 13.1; 202/236, 173, 187

[56] References Cited

U.S. PATENT DOCUMENTS

| | | | |
|---|---|---|---|
| 2,547,938 | 4/1951 | Hall et al. | 568/576 |
| 2,706,708 | 4/1955 | Frank et al. | 203/92 |
| 2,722,506 | 11/1955 | Ellis | 568/576 |
| 2,735,871 | 2/1956 | Smith | 568/576 |
| 3,049,477 | 8/1962 | Cooke | 203/69 |
| 3,092,587 | 6/1963 | Ester et al. | 203/72 |
| 3,519,690 | 7/1970 | Joris et al. | 568/576 |
| 4,316,767 | 2/1982 | Saida et al. | 159/49 |

FOREIGN PATENT DOCUMENTS 843032  8/1960  United Kingdom ............... 568/576

Primary Examiner—Wilbur Bascomb
Attorney, Agent, or Firm—William L. Krayer

[57] ABSTRACT

Crude cumene hydroperoxide is purified by subjecting it to an evaporation step at a pressure of about 2 to 10 (preferably 3 to 7) mg Hg abs. and a temperature of about 150° F. to about 210° F. (pref. about 175° F. to 195° F.) to remove light impurities and then subjecting the residue from the first evaporation step to a second evaporation step also at a temperature of about 135° F. to 210° F. (pref. about 150° F. to 185° F.) but at a pressure of about 0.5 to about 8 (preferably 1 to 3) mm Hg abs. to obtain a distillate significantly reduced in color bodies, water, acetophenone, and dimethylbenzyl alcohol, and sodium.

7 Claims, 2 Drawing Figures

PURIFYING CUMENE HYDROPEROXIDE

This application is a continuation-in-part of co-pending application U.S. Ser. No. 780,756, filed Sept. 27, 1985, now abandoned and incorporated herein.

TECHNICAL FIELD

This invention relates to the refining of cumene hydroperoxide.

In a common commercial process of making phenol, cumene is first oxidized to cumene hydroperoxide (CHP) in the presence of excess cumene. The excess cumene is then stripped from the CHP and recycled to oxidation. Normally the bulk of the CHP product is cleaved, by the influence of an acid catalyst, to form phenol and acetone, which along with some by-products are subsequently fractionated to the final products. A smaller portion of the CHP may be used for purposes requiring greater purity, however. Such use demands the removal of significant portions of the water, acetophenone, and dimethylbenzyl alcohol, as well as unidentified color bodies. However, during oxidation some of the cumene is oxidized to acetophenone and dimethylbenzyl alcohol (AP and DMBA) rather than to CHP. These components along with unstripped cumene contaminate the product. Also the cumene stripping may be done with steam and aqueous alkali solutions can be employed in the oxidation step. This would result in more water in the product than some customers can tolerate. Moreover in oxidation unidentified color bodies are formed, resulting in a CHP product that sometimes has a color greater than APHA 500, an unacceptably high value. In short, the CHP product tends to suffer from high water content, low purity and high color. Separation or removal of the CHP from the mixture has been difficult in the past because the thermal instability to cumene hydroperoxide would seem to preclude many of the possible approaches.

BACKGROUND ART

Of interest in the manufacture of cumene hydroperoxide from cumene are U.S. Pat. Nos. 2,547,938, 2,706,708, 2,722,506, and 3,049,477, all of which relate primarily to the concentration of CHP in a manufacturing process to obtain a product which is more or less of the composition of our starting material. Of particular note may be the steps followed in the example in U.S. Pat. No. 3,049,477, which include the use of a climbing film evaporator. Of perhaps more relevance to our objectives are U.S. Pat. Nos. 2,735,871 and 3,519,690, which are directed to purifying a concentrated CHP stream; however, the approaches used by the inventors are completely different from ours.

DISCLOSURE OF INVENTION

We have found that a crude CHP product can be subjected to a two-step evaporation which yields a clearly superior CHP product, while operating in such a manner as to minimize the substantial hazards of a thermally-induced, uncontrolled decomposition. In this process a crude CHP product first is evaporated at a pressure of 2 to 10 mm Hg abs. and a temperature of 150° to 210° F. The amount of distillate may be varied as desired, but we have found that removing about 20% to 45% of the feed as distillate provides sufficient reduction of light impurities in the final CHP product. This distillate which is primarily CHP will contain most of the water and cumene and a portion of the AP and DMBA that was in the feed but essentially all of the color bodies will remain with the residue. Thus by subjecting a feed containing 1.0% water, 2.1% cumene, 6.9% DMBA, 1.3% AP, 88.8% CHP and an APHA color of >200 to the evaporation step described above, a residue was produced containing <0.1% water, 0.2% cumene, 5.5% DMBA, 0.9% AP, 93.5% CHP and an APHA color of >200. We have further found that this residue can be subjected to a second evaporation step at a pressure of 0.5 to 8 mm Hg abs. and a temperature of 135° F. to 210° F. and that about 60%–80% of the feed may be evaporated away from the color-bodies which remain in the residue. The light impurities will increase an acceptably slight amount, but since the color bodies are relatively non-volatile the distillate will be much improved in color. Thus by subjecting a feed that is similar in composition to the first evaporator residue— namely 0.2% water, 0.2% cumene, 5.0% DMBA, 0.8% AP, 93.8% CHP and color of 200–300 to the 2 mm Hg evaporation, a distillate was obtained containing 0.1% water, 0.1% cumene, 6.3% DMBA, 1.1% AP, 92.4% CHP and color of 30–40. Moreover the crude CHP may contain sodium, typically about 20–40 ppm sodium (in the form of a salt or complex) when sodium is used in the oxidation step. Since the sodium is essentially non-volatile, it will be greatly reduced in the final distilate product. In the above example the sodium in the initial feed measured 27 ppm and the sodium in the final distillate product measured 1.1 ppm. Sodium in the CHP is considered undesirable by some users. Thus by subjecting a crude CHP feed that was low in CHP purity, high in water, high in color and high in sodium to this two-step evaporation process, a CHP product was produced that had none of these shortcomings.

The evaporation temperature was limited to 220° F. or less because CHP is thermally unstable and its temperature is maintained below 235° F. for safety reasons. The low operating temperature requires that the process be conducted under vacuum, namely less than 10 mm Hg. Also, the temperature of the heating medium was maintained below 235° F. to ensure that the CHP would not be overheated even in the event of a blockage of flow. Additionally, the evaporation step was carried out in an apparatus which provides a minimum exposure time to the heat. Given these limitations, it would not be expected that a process could be developed which would result in a substantially improved CHP product in both a safe and economical manner. Also, it is not at all obvious that the color bodies could be separated by simple evaporation in the second step.

Our invention comprises refining the cumene hydroperoxide product stream containing, in weight percents, about 80 to about 89 CHP, about 0.6 to about 1.6 water, about 0.5 to about 2.0 acetophenone, about 2 to about 15 cumene, and about 5 to about 9 dimethylbenzyl alcohol by subjecting it to a first evaporation step at a temperature of 150° F. to 210° F. and pressure of 2 to 10 mm Hg, passing the residue therefrom to a second evaporation step at a temperature of about 135° to about 210° F. and a pressure of about 0.5 to about 8 mm Hg, and condensing the vapors therefrom to recover a refined cumene hydroperoxide.

BEST MODE FOR CARRYING OUT THE INVENTION

The commercial evaporation process can be conducted advantageously in a wiped-film evaporator. This type of evaporator minimizes liquid inventory and hence minimizes safety concerns, and it also does not cause any elevation in boiling point due to hydrostatic head which could suppress vaporization. This type of evaporator may also be equipped with an internal condenser, which minimizes the pressure drop between the evaporating and condensing surfaces and thus is advantageous at low operating pressures. However, any other type of evaporator, such as a falling film evaporator, which obtains similar advantages would be equally acceptable. Hence the use of the wiped-film evaporator is for example only.

Our invention is of course not limited to the specific conditions recited above.

The composition of the feed may vary as follows:

| | |
|---|---|
| water | 0.6 to 1.6% |
| cumene | 2 to 15% |
| DMBA | 5 to 9% |
| AP | 0.5 to 2% |
| CHP | 80 to 89% |
| APHA color | 100 to >500 |

The pressure and temperature we employ may vary between 2 to 10 mm Hg (preferably 3 to 7 mm Hg) and 155° to 210° F. (preferably 175° to 195° F.) in the first evaporator. The amount of distillate removed may be varied according to the degree of lights removal required or economically justified, but we have found that removing about 20% to 45% of the feed as distillate provides an adequate reduction of light impurities in the final CHP product.

Compositions of the above ingredients within the above ranges may be expected to yield residues having compositions as follows:

<0.1–0.1% water
0.1–0.5% cumene
2.5–6.0% DMBA
0.4–1.0% AP
92.0%–95.2% CHP
APHA color >200

Such residues may be used in the second evaporator at pressures of 0.5 to B 8 mm Hg (preferably 1 to 3 mm Hg) and temperatures of 135° to 210° F. (preferably 150° to 185° F.). The amount of product removed as distillate may be varied according to the degree of color removal required. It may also be desirable to include some means of reducing entrainment of the mostly non-volatile color-bodies from the highly colored residue into the distillate product. Under these conditions, including the use of a suitable entrainment separator, we have found that evaporating about 60%–80% of the feed gives a product of good color (<50 APHA) and at a reasonable yield. The product from this step may be expected to have a purity of 90.1%–92.4% CHP, e.g. of the following composition:

| | |
|---|---|
| water | 0.1 to 0.2% |
| cumene | 0.1 to 0.4% |
| DMBA | 5.0 to 7.1% |
| AP | 0.6 to 1.2% |
| CHP | 90.1 to 92.4% |
| APHA color | <50 |
| Na | <2 ppm |

Although the CHP product may contain 90.1 to 92.4 wt.% CHP, this concentration may be too high for certain intended uses. Indeed, shipment by tank cars is limited by regulation to CHP concentrations of no more than 90%. In these cases, it may be desirable to reduce the CHP concentration by adding cumene to the concentrated product.

BRIEF DESCRIPTION OF THE DRAWINGS

A preferred apparatus for use in the two-stage evaporation is shown in FIG. 1. A preferred system for the process is illustrated more or less diagrammatically in FIG. 2.

Figure 1:
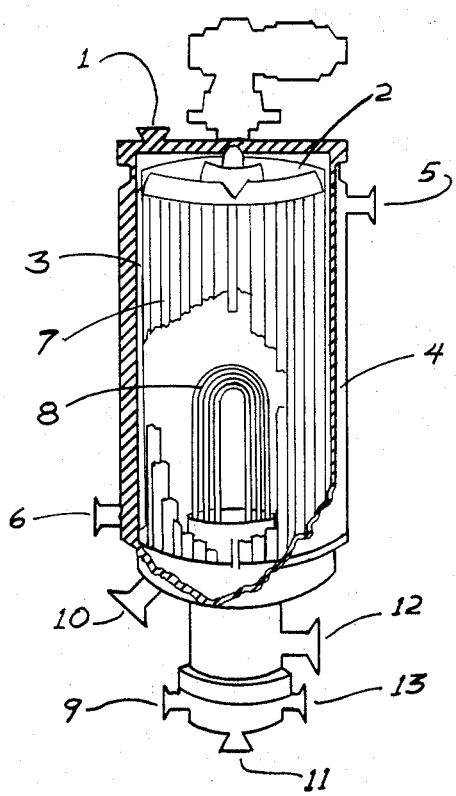
FIG. 1 shows the major components of the preferred apparatus, namely a wiped-film evaporator equipped with an internal condenser. Crude CHP enters at the feed inlet 1 where it is directed to the walls by distributor plate 2. The feed is spread into a thin film by the action of the wipers 3, which also assist in moving the feed down the heated wall. The heat is provided by steam, which enters the heated jacket 4 at inlet 5, with the steam condensate leaving at outlet 6. Entrainment is reduced by entrainment separators 7, when used. The distillate which evaporates from the wall is condensed on the internal condenser 8, which typically will have multiple tubes. Cooling water for the condenser enters at inlet 13 and leaves at outlet 9. The residue from the wall leaves the evaporator at the residue outlet 10. The condensed distillate leaves through the distillate outlet 11. Vacuum is provided via the vapor outlet 12.
Figure 2:
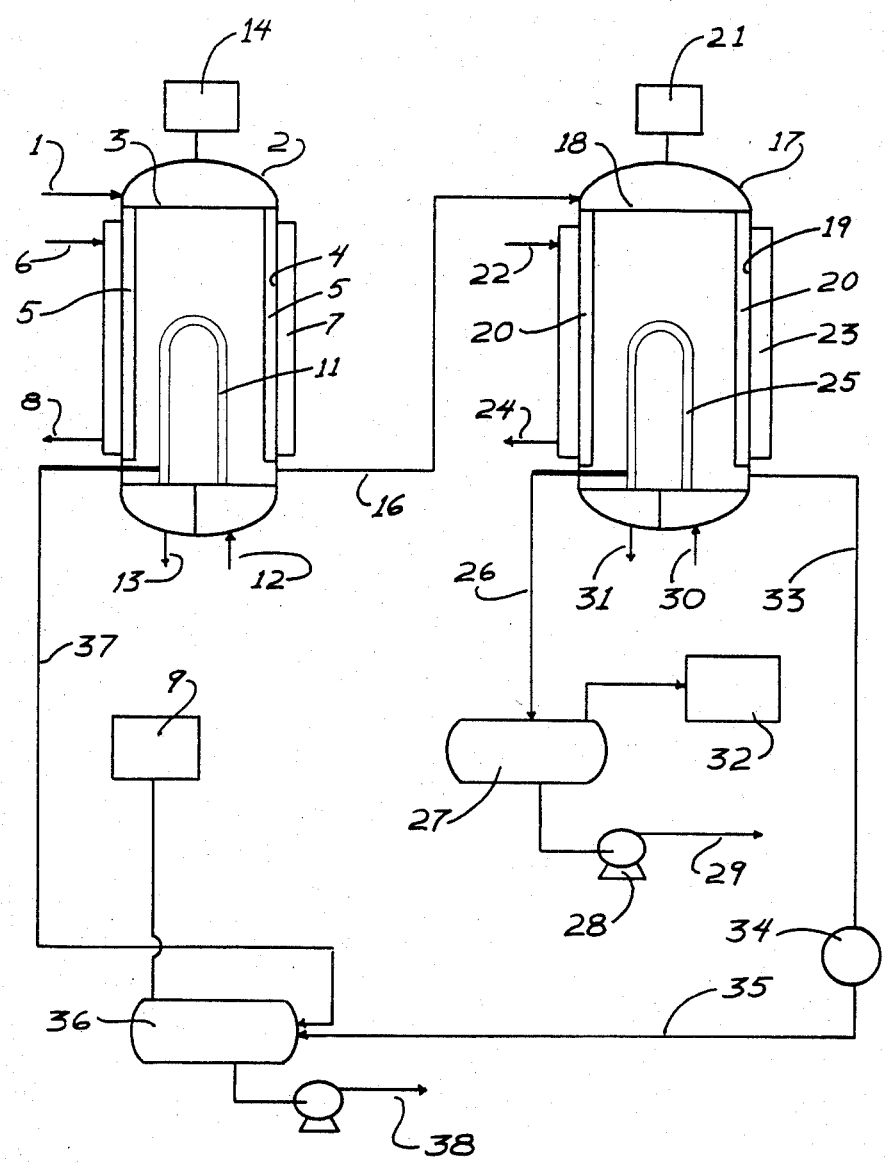
In FIG. 2, a system for producing about 3 gpm of refined CHP product is shown. Crude CHP in line 1 is sent to a first wiped-film evaporator 2 which operates at 5 mm Hg and 189° F. Liquid enters the distributor 3, from where it flows down the wall 4 via the action of the wiper blades 5, which are driven by the motor 14. The heat is provided by steam from line 6 at a pressure of 3 to 4 psig which enters the heating jacket 7. The condensed steam leaves through line 8. The vapor containing the light impurities is condensed on the internal condenser 11 and leaves by line 37. Cooling water is provided to the condenser through line 12 and leaves by line 13. Vacuum is provided by source 9. The residue from the first evaporator 2 flows through line 16 to a second wiped-film evaporator 17 operating at 2 mm Hg and 173° F. Liquid enters the distributor 18, from where it flows down the wall 19 via the action of the wiper blades 20, which are driven by the motor 21. The heat is provided by steam from line 22 at a pressure of 3 to 4 psig which enters the heating jacket 23. The condensed steam leaves through line 24. The vapor, constituting the refined CHP product, is condensed on the internal condenser 25 and is conducted by line 26 to accumulator vessel 27, from where it may be removed by pump 28 for shipment through line 29. Cooling water is provided to the condenser through line 30 and leaves by line 31. Vacuum is provided by source 32. The residue from the second evaporator 17 is conducted by line 33 to cooler 34 before flowing through line 35 to accumulator 36, where it may be combined with the condensed vapors 37 from the first evaporator 2. The material in the accumulator 36 may be sent to cleavage through line 38 along with the main CHP flow from other parts of the plant not shown.

The wiped-film evaporator has some definite advantages for performing the two-stage evaporation, due to its low residence time which minimizes exposure to the heat and the wiped-film which enhances heat transfer at the low temperature differences employed between the heating medium and the CHP. The internal condenser also is advantageous for the evaporation steps since it decreases the pressure drop, thus reducing the expense of achieving the low pressures required in the process. However, we do not intend to limit the apparatus to a wiped-film evaporator with an internal condenser—any other system that achieves similar advantages would be equally applicable.

A system similar to that shown in the drawing was used to generate the data in Table I. Table I lists experimental results for the first-stage evaporation step. All feed for the first stage was crude CHP from a commercial phenol plant.

Table II lists experimental results for the second-stage evaporation step. The feed for the second stage was provided by the bottoms products from the first-stage evaporation steps, as noted in the Table.

TABLE I

CHP Purification Experimental Results
FIRST PASS - Feed:Crude CHP from a Phenol Plant

| Run # | Press. mm Hg | Est'd. Temp. °F. | % Dist. | Stream Rate lb/hr | Wt. % Composition DMBA | Cumene | AP | CHP | Water | PPM Sodium | APHA Color | Stream Name |
|---|---|---|---|---|---|---|---|---|---|---|---|---|
| 3 | 9.0 | 219.0 | 65.5 | 108.8 | 6.66 | .83 | 1.14 | 90.77 | 0.6 | 16 | 200–300 | Feed |
|   |   |   |   | 71.3 | 9.50 | 1.16 | 1.67 | 87.27 | 0.4 |   |   | Distillate |
|   |   |   |   | 37.5 | 3.23 | 0.30 | 0.42 | 96.05 | <0.1 |   |   | Residue |
| 5 | 7.0 | 208.8 | 49.4 | 118.7 | 6.66 | .83 | 1.14 | 90.77 | 0.6 | 16 | 200–300 | Feed |
|   |   |   |   | 58.7 | 9.89 | 1.19 | 1.75 | 86.77 | 0.4 |   |   | Distillate |
|   |   |   |   | 60.0 | 3.51 | 0.28 | 0.51 | 95.70 | <0.1 |   |   | Residue |
| 6 | 8.0 | 207.3 | 20.5 | 220.0 | 6.66 | 0.83 | 1.14 | 90.77 | 0.6 | 16 | 200–300 | Feed |
|   |   |   |   | 45.0 | 12.03 | 2.49 | 2.26 | 82.62 | 0.6 |   |   | Distillate |
|   |   |   |   | 175.0 | 5.12 | 0.23 | 0.82 | 93.83 | <0.1 |   |   | Residue |
| 7 | 8.0 | 208.3 | 22.9 | 185.0 | 6.66 | 0.83 | 1.14 | 90.77 | 0.6 | 16 | 200–300 | Feed |
|   |   |   |   | 42.5 | 12.42 | 2.44 | 2.33 | 82.22 | 0.6 |   |   | Distillate |
|   |   |   |   | 142.5 | 5.04 | 0.20 | 0.78 | 93.98 | <0.1 |   |   | Residue |
| 8 | 7.5 | 206.6 | 24.5 | 183.8 | 6.66 | 0.83 | 1.14 | 90.77 | 0.6 | 16 | 200–300 | Feed |
|   |   |   |   | 45.0 | 11.98 | 2.20 | 2.23 | 82.89 | 0.7 |   |   | Distillate |
|   |   |   |   | 138.8 | 4.95 | 0.21 | 0.77 | 94.07 | <0.1 |   |   | Residue |
| 9 | 7.5 | 207.9 | 28.9 | 168.8 | 6.66 | 0.83 | 1.14 | 90.77 | 0.6 | 16 | 200–300 | Feed |
|   |   |   |   | 48.8 | 11.85 | 2.21 | 2.21 | 83.14 | 0.6 | 1.6 |   | Distillate |
|   |   |   |   | 120.0 | 4.74 | 0.22 | 0.76 | 94.28 | <0.1 | 20 | 300–400 | Residue |
| 10 | 7.5 | 207.9 | 29.2 | 186.4 | 6.66 | 0.83 | 1.14 | 90.77 | 0.6 | 16 | 200–300 | Feed |
|   |   |   |   | 54.4 | 11.33 | 1.83 | 2.11 | 84.54 | 0.2 | 1.4 |   | Distillate |
|   |   |   |   | 132.0 | 4.87 | 0.25 | 0.86 | 94.02 | <0.1 | 30 | >400 | Residue |
| 12 | 17 | 209.1 | 3.3 | 113.8 | 6.66 | 0.83 | 1.14 | 90.77 | 0.6 | 16 | 200–300 | Feed |
|   |   |   |   | 3.8 | 13.84 | 6.64 | 2.77 | 75.05 | 1.7 |   |   | Distillate |
|   |   |   |   | 110.0 | 6.46 | 0.30 | 1.12 | 92.12 | <0.1 |   |   | Residue |
| 13 | 6.0 | 205.8 | 76.6 | 117.5 | 6.28 | 0.58 | 1.09 | 91.45 | 0.6 | 21 | 300–400 | Feed |
|   |   |   |   | 90.0 | 8.38 | 0.77 | 1.47 | 89.18 | 0.2 |   |   | Distillate |
|   |   |   |   | 27.5 | 3.29 | 0.47 | 0.46 | 95.78 | <0.1 |   |   | Residue |
| 14 | 6.0 | 201.7 | 33.3 | 180.0 | 6.28 | 0.58 | 1.09 | 91.45 | 0.6 | 21 | 300–400 | Feed |
|   |   |   |   | 60.0 | 10.14 | 1.37 | 1.90 | 86.49 | 0.1 |   |   | Distillate |
|   |   |   |   | 128.0 | 4.61 | 0.20 | 0.71 | 94.48 | <0.1 |   |   | Residue |
| 15 | 6.0 | 203.9 | 49.4 | 144.4 | 6.28 | 0.58 | 1.09 | 91.45 | 0.6 | 21 | 300–400 | Feed |
|   |   |   |   | 71.3 | 10.36 | 1.01 | 1.88 | 86.65 | 0.1 |   |   | Distillate |
|   |   |   |   | 73.1 | 3.84 | 0.22 | 0.56 | 95.28 | 0.1 |   |   | Residue |
| 16 | 6.0 | 202.2 | 36.5 | 171.3 | 6.28 | 0.58 | 1.09 | 91.45 | 0.6 | 21 | 300–400 | Feed |
|   |   |   |   | 62.5 | 11.04 | 1.25 | 2.05 | 85.56 | 0.1 |   |   | Distillate |
|   |   |   |   | 108.8 | 4.04 | 0.18 | 0.61 | 95.17 | <0.1 |   |   | Residue |
| 17 | 6.0 | 201.7 | 33.3 | 213.8 | 6.28 | 0.58 | 1.09 | 91.45 | 0.6 | 21 | 300–400 | Feed |
|   |   |   |   | 71.3 | 11.77 | 1.53 | 2.22 | 84.39 | 0.1 |   |   | Distillate |
|   |   |   |   | 142.5 | 4.23 | 0.18 | 0.66 | 94.93 | <0.1 |   |   | Residue |
| 18 | 6.0 | 200.0 | 25.4 | 251.3 | 6.28 | 0.58 | 1.09 | 91.45 | 0.6 | 21 | 300–400 | Feed |
|   |   |   |   | 63.8 | 11.95 | 1.90 | 2.28 | 83.78 | 0.1 |   |   | Distillate |
|   |   |   |   | 187.5 | 4.72 | 0.17 | 0.75 | 94.27 | 0.1 |   |   | Residue |
| 19 | 7.0 | 198.1 | 24.0 | 187.5 | 6.91 | 2.08 | 1.25 | 88.76 | 1.0 | 22 | 200–300 | Feed |
|   |   |   |   | 45.0 | 12.03 | 5.26 | 2.44 | 79.68 | 0.6 |   | 60–70 | Distillate |
|   |   |   |   | 142.5 | 5.57 | 0.22 | 0.95 | 93.16 | 0.1 |   |   | Residue |
| 20 | 7.0 | 201.4 | 31.8 | 170.7 | 6.91 | 2.08 | 1.25 | 88.76 | 1.0 | 22 | 200–300 | Feed |
|   |   |   |   | 54.4 | 12.24 | 4.35 | 2.43 | 80.58 | 0.4 |   |   | Distillate |
|   |   |   |   | 116.3 | 5.46 | 0.22 | 0.88 | 93.46 | <0.1 |   |   | Residue |
| 21 | 7.5 | 202.3 | 28.1 | 166.9 | 6.91 | 2.08 | 1.25 | 88.76 | 1.0 | 22 | 200–300 | Feed |
|   |   |   |   | 46.9 | 12.67 | 4.65 | 2.56 | 79.63 | 0.5 |   | 50–60 | Distillate |
|   |   |   |   | 120.0 | 5.37 | 0.19 | 0.88 | 93.56 | <0.1 |   |   | Residue |
| 22 | 7.5 | 200.1 | 34.9 | 161.3 | 6.91 | 2.08 | 1.25 | 88.76 | 1.0 | 22 | 200–300 | Feed |
|   |   |   |   | 56.3 | 12.63 | 4.00 | 2.50 | 80.38 | 0.5 |   |   | Distillate |
|   |   |   |   | 105.0 | 5.65 | 0.23 | 0.88 | 93.24 | 0.1 |   |   | Residue |
| 23 | 7.5 | 200.1 | 23.3 | 205.4 | 6.91 | 2.08 | 1.25 | 88.76 | 1.0 | 22 | 200–300 | Feed |
|   |   |   |   | 47.9 | 12.48 | 5.15 | 2.53 | 79.45 | 0.4 |   |   | Distillate |
|   |   |   |   | 157.5 | 5.84 | 0.20 | 0.97 | 92.98 | <0.1 |   |   | Residue |
| 24 | 7.5 | 199.8 | 22.8 | 213.8 | 6.91 | 2.08 | 1.25 | 88.76 | 1.0 | 22 | 200–300 | Feed |
|   |   |   |   | 48.8 | 12.83 | 5.51 | 2.61 | 78.45 | 0.6 |   |   | Distillate |
|   |   |   |   | 165.0 | 5.54 | 0.24 | 0.93 | 94.29 | <0.1 |   |   | Residue |
| 25 | 7.5 | 199.0 | 21.5 | 205.4 | 6.91 | 2.08 | 1.25 | 88.76 | 1.0 | 22 | 200–300 | Feed |
|   |   |   |   | 44.1 | 12.81 | 5.60 | 2.62 | 78.57 | 0.4 |   |   | Distillate |
|   |   |   |   | 161.3 | 5.82 | 0.20 | 0.98 | 93.00 | <0.1 |   |   | Residue |
| 26 | 7.5 | 201.3 | 25.6 | 206.7 | 6.91 | 2.08 | 1.25 | 88.76 | 1.0 | 22 | 200–300 | Feed |
|   |   |   |   | 52.9 | 13.35 | 5.43 | 2.71 | 77.91 | 0.6 |   |   | Distillate |
|   |   |   |   | 153.8 | 5.75 | 0.19 | 0.93 | 93.13 | <0.1 |   |   | Residue |
| 27 | 7.5 | 197.5 | 19.3 | 241.6 | 6.91 | 2.08 | 1.25 | 88.76 | 1.0 | 22 | 200–300 | Feed |

TABLE I-continued

CHP Purification Experimental Results
FIRST PASS - Feed:Crude CHP from a Phenol Plant

| Run # | Press. mm Hg | Est'd. Temp. °F. | % Dist. | Stream Rate lb/hr | Wt. % Composition DMBA | Cumene | AP | CHP | Water | PPM Sodium | APHA Color | Stream Name |
|---|---|---|---|---|---|---|---|---|---|---|---|---|
|  |  |  |  | 46.6 | 13.44 | 6.47 | 2.77 | 76.82 | 0.5 |  |  | Distillate |
|  |  |  |  | 195.0 | 5.78 | 0.20 | 0.99 | 93.03 | <0.1 |  |  | Residue |
| 28 | 7.5 | 196.7 | 18.2 | 247.5 | 6.91 | 2.08 | 1.25 | 88.76 | 1.0 | 22 | 200–300 | Feed |
|  |  |  |  | 45.0 | 12.17 | 6.56 | 2.55 | 78.12 | 0.6 |  |  | Distillate |
|  |  |  |  | 202.5 | 6.24 | 0.22 | 1.02 | 92.52 | <0.1 |  |  | Residue |
| 29 | 7.5 | 188.5 | 11.1 | 316.3 | 6.91 | 2.08 | 1.25 | 88.76 | 1.0 | 22 | 200–300 | Feed |
|  |  |  |  | 35.0 | 13.61 | 9.02 | 2.86 | 73.72 | 0.8 |  |  | Distillate |
|  |  |  |  | 281.3 | 6.76 | 0.27 | 1.14 | 91.83 | <0.1 |  |  | Residue |

TABLE II

CHP Purification Experimental Results
SECOND PASS - Feed:Mixture of Residue from Runs 27 & 28

| Run # | Press. mm Hg | Est'd. Temp. °F. | % Dist. | Stream Rate lb/hr | Wt. % Composition DMBA | Cumene | AP | CHP | Water | PPM Sodium | APHA Color | Stream Name |
|---|---|---|---|---|---|---|---|---|---|---|---|---|
| 30 | 5.0 | 202.6 | 88.1 | 68.1 | 5.03 | 0.17 | 0.81 | 93.84 | .15 | 27 | 200–300 | Feed |
|  |  |  |  | 60.0 | 6.14 | 0.25 | 1.04 | 92.44 | (0.1) |  | 40–50 | Distillate |
|  |  |  |  | 8.1 | 3.38 | 0.75 | 0.44 | 95.33 | (0.1) |  |  | Residue |
| 31 | 5.0 | 202.4 | 70.6 | 127.5 | 5.03 | 0.17 | 0.81 | 93.84 | .15 | 27 | 200–300 | Feed |
|  |  |  |  | 90.0 | 6.55 | 0.10 | 1.12 | 92.04 | 0.2 |  | 20–30 | Distillate |
|  |  |  |  | 37.5 | 2.26 | 0.40 | 0.25 | 96.99 | (0.1) |  |  | Residue |
| 32 | 5.0 | 202.1 | 54.3 | 186.3 | 5.03 | 0.17 | 0.81 | 93.84 | .15 | 27 | 200–300 | Feed |
|  |  |  |  | 101.3 | 8.08 | 0.32 | 1.44 | 90.06 | (0.1) |  | 10–20 | Distillate |
|  |  |  |  | 85.0 | 3.23 | 0.29 | 0.42 | 95.96 | (0.1) |  |  | Residue |
| 33 | 5.0 | 201.7 | 42.1 | 213.8 | 5.03 | 0.17 | 0.81 | 93.84 | .15 | 27 | 200–300 | Feed |
|  |  |  |  | 90.0 | 9.13 | 0.15 | 1.63 | 88.99 | (0.1) |  | 10–20 | Distillate |
|  |  |  |  | 123.8 | 3.40 | 0.22 | 0.48 | 95.80 | (0.1) |  |  | Residue |
| 34 | 5.0 | 202.0 | 51.4 | 175.0 | 5.03 | 0.17 | 0.81 | 93.84 | .15 | 27 | 200–300 | Feed |
|  |  |  |  | 90.0 | 8.27 | 0.12 | 1.46 | 90.05 | (0.1) |  | 20–30 | Distillate |
|  |  |  |  | 85.0 | 3.05 | 0.26 | 0.41 | 96.18 | (0.1) |  |  | Residue |
| 35 | 5.0 | 202.2 | 61.0 | 147.5 | 5.03 | 0.17 | 0.81 | 93.84 | .15 | 27 | 200–300 | Feed |
|  |  |  |  | 90.0 | 6.81 | 0 | 1.18 | 91.91 | (0.1) |  | 30–40 | Distillate |
|  |  |  |  | 57.5 | 2.27 | 0.29 | 0.29 | 97.05 | 0.1 |  |  | Residue |
| 36 | 2.0 | 173.1 | 73.8 | 236.3 | 5.03 | 0.17 | 0.81 | 93.84 | .15 | 27 | 200–300 | Feed |
|  |  |  |  | 174.4 | 6.41 | 0.14 | 1.09 | 92.26 | 0.1 | 1.1 | 30–40 | Distillate |
|  |  |  |  | 61.9 | 2.29 | 0.39 | 0.25 | 96.97 | 0.1 | 102 |  | Residue |
| 37 | 2.0 | 173.0 | 68.3 | 248.0 | 5.03 | 0.17 | 0.81 | 93.84 | .15 | 27 | 200–300 | Feed |
|  |  |  |  | 170.0 | 6.33 | 0.09 | 1.09 | 92.39 | 0.1 |  | 30–40 | Distillate |
|  |  |  |  | 78.8 | 2.40 | 0.36 | 0.27 | 96.87 | 0.1 |  |  | Residue |
| 38 | 2.0 | 173.0 | 66.3 | 256.3 | 5.03 | 0.17 | 0.81 | 93.84 | .15 | 27 | 200–300 | Feed |
|  |  |  |  | 170.0 | 7.16 | 0.10 | 1.23 | 91.41 | (0.1) |  | 20–30 | Distillate |
|  |  |  |  | 86.3 | 2.74 | 0.32 | 0.32 | 96.82 | (0.1) |  |  | Residue |
| 39 | 2.0 | 172.7 | 53.3 | 304.0 | 5.03 | 0.17 | 0.81 | 93.84 | .15 | 27 | 200–300 | Feed |
|  |  |  |  | 162.5 | 6.78 | 0.08 | 1.20 | 91.84 | (0.1) |  | 20–30 | Distillate |
|  |  |  |  | 142.5 | 3.48 | 0.66 | 0.46 | 95.30 | (0.1) |  |  | Residue |

We claim:

1. In the manufacture of cumene hydroperoxide (CHP) wherein cumene is oxidized to CHP, the improvement comprising refining the cumene hydroperoxide product stream containing, in weight percents, about 80 to about 89 CHP, about 0.6 to about 1.6 water, about 0.5 to about 2.0 acetophenone, about 2 to about 15 cumene, and about 5 to about 9 dimethylbenzyl alcohol to obtain a product substantially reduced in color, water, acetophenone, and dimethylbenzyl alcohol, by subjecting said product stream to a first evaporation step at a temperature of 150° to 210° F. and pressure of 2 to 10 mm Hg, passing the residue therefrom to a second evaporation step at a temperature of about 135° to about 210° F. and a pressure of about 0.5 to about 8 mm Hg, and condensing the vapors therefrom to recover a refined cumene hydroperoxide.

2. Method of claim 1 wherein the first evaporation step is performed at 3 to 7 mm Hg and 175° to 195° F. and the second evaporation step is performed at 1 to 3 mm Hg and 150° to 185° F.

3. Method of claim 1 wherein the first evaporation step is conducted in an evaporative system which minimizes exposure to heat and provides efficient heat transfer at a low temperature difference.

4. Method of claim 1 wherein the first and second evaporation steps are performed in a wiped-film evaporator.

5. Method of claim 1 wherein the product is reduced in color to <50 APHA.

6. Method of claim 1 wherein the feed stream also contains about 20–40 ppm of sodium, which is substantially reduced in the product obtained.

7. Method of claim 1 wherein the first and second evaporation steps are performed in a wiped-film evaporator with an internal condenser to minimize pressure drop.

* * * * *

UNITED STATES PATENT AND TRADEMARK OFFICE
CERTIFICATE OF CORRECTION

PATENT NO. : 4,654,124

DATED : 3-31-87

INVENTOR(S) : Carole L. Elias and Marvin C. Fields

It is certified that error appears in the above-identified patent and that said Letters Patent is hereby corrected as shown below:

Column 3, line 42, before "8 mm Hg", delete the letter -- B --.

Signed and Sealed this

Thirteenth Day of October, 1987

Attest:

DONALD J. QUIGG

Attesting Officer     Commissioner of Patents and Trademarks